Figure 1A:
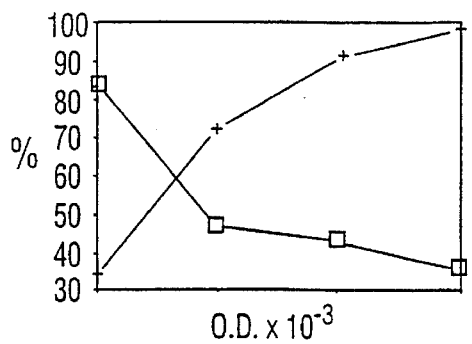

United States Patent [19]
Laszlo et al.

[11] Patent Number: 5,597,735
[45] Date of Patent: *Jan. 28, 1997

[54] GLYCOLIPIDS FOR SERODIAGNOSIS OF TUBERCULOSIS AND LEPROSY

[75] Inventors: Adalbert Laszlo; Vera Handzel, both of Nepean; Lucio Vera-Cabrera, Ottawa, all of Canada

[73] Assignee: Her Majesty the Queen in right of Canada, as represented by the Minister of Health and Welfare, Ottawa, Canada

[ * ] Notice: The term of this patent shall not extend beyond the expiration date of Pat. No. 5,344,759.

[21] Appl. No.: 300,268

[22] Filed: Sep. 2, 1994

Related U.S. Application Data

[63] Continuation-in-part of Ser. No. 881,193, May 11, 1992, Pat. No. 5,344,759.

[51] Int. Cl.$^6$ ............... G01N 33/553; G01N 33/544; G01N 33/00
[52] U.S. Cl. ............... 436/525; 436/530; 436/87; 436/811; 436/828; 435/975
[58] Field of Search ............... 435/7.32, 7.92, 435/7.95; 436/518, 530, 525, 828; 536/53, 115, 119

[56] References Cited

U.S. PATENT DOCUMENTS 4,962,023  10/1990  Todd et al. ............... 436/518
5,344,759   9/1994  Loszlo et al. ............... 435/7.2

OTHER PUBLICATIONS

Harlow et al, "Antibodies a Laboratory Manual" by Cold Spring Harbor Laboratory, NY, 1988 p. 175.
Sidberry et al, Journal of Immunological Methods 76:299–305, 1985.
Herbrink et al, Journal of Immunological Methods 48:293–298, 1982.
Cruad et al, Res. Microbiol, 141:679–694, 1990.
Papa et al, Acta Leprologica, 7(Suppl. 1):98–101, 1989.
Goren et al, Chemistry and Physics of Lipids 25:209–224, 1979.
Baer et al, Carbohydrate Research, 200:377–389, 1990.

*Primary Examiner*—Marian C. Knode
*Assistant Examiner*—Patricia A. Duffy
*Attorney, Agent, or Firm*—J. Wayne Anderson

[57] ABSTRACT

A Dot-Blot assay ("spot test") with Bis-N,N,dioctadecylamide (BDA.TDA) as antigen was developed to detect anti-BDA.TDA antibodies in tuberculosis patients. To develop the antigen-antibody reaction, as a first step and in order to enhance the reaction, an anti-human rabbit serum was used followed by incubation with a protein A-colloidal gold conjugate. This assay showed almost equal sensitivity and specificity as the β-galactosidase ELISA test which was conducted in parallel. This simple and fast assay could be used in places where ELISA equipment is not easily available.

3 Claims, 5 Drawing Sheets

1 R = OH, R' = H ("TREHALOSE DICARBOXYLIC ACID")
2 R = OCH$_3$, R'= H
3 R = OH, R' = CH$_3$CO -
4 R = Cl, R' = CH$_3$CO -

TDA BIS DI-N-OCTADECYLAMIDE
R = C₁₈H₃₇
"MIRROR AMIDE" PSEUDO CORD FACTOR

GLYCOLIPIDS FOR SERODIAGNOSIS OF TUBERCULOSIS AND LEPROSY

This application is a continuation-in-part of applicant's U.S. application Ser. No. 07/881,193 filed 11 May 1992, now U.S. Pat. No. 5,344,759.

BACKGROUND OF THE INVENTION

I. Field of the Invention

This invention relates to glycolipids useful for serodiagnosis of tuberculosis and leprosy and to serodiagnosis techniques using such glycolipids. More particularly, the invention relates to synthetic pseudo cord factor-like glycolipids useful for these purposes.

II. Description of the Prior Art

Enzyme-linked immunosorbant assays (usually referred to as ELISA) and similar techniques (e.g. so-called "spot tests" which are a simplified form of ELISA test) for diagnosing diseases in human and animal patients have become very useful and popular in recent years because of their simplicity and their acceptable sensitivity and specificity. These techniques are based on the binding effects of antibodies and antigens. In one form of the ELISA assay, for example, an antigen produced by a specific organism is used to test for the presence of antibodies for the antigen in the sera of patients, thus providing an indication that the patients have been exposed to these organisms. The antigen is immobilized on a solid support and incubated with the serum to be tested. If a target antibody is present in the serum, indicating exposure of the patient to the disease-causing organism, it binds to the layer of antigen. The number of antigen/antibody bound molecular pairs produced in this way depends on the concentration of the antibody in the serum until saturation of the antigens in the layer takes place. After washing the layer attached to the support, a solution of an enzyme-linked antibody (e.g. goat-antihuman IgG) for the bound protein is contacted with the supported layer. After a second washing step, the layer is contacted with a solution of a substrate for the enzyme and the bound enzyme, if present, converts the substrate to a detectable product.

In the so-called "spot tests", the microtiter plate usually used as a solid support for the antigen in the ELISA test is replaced by a strip of paper (cellulose nitrate, etc.). The strip is spotted with the antigen and for instance Protein A is used instead of the conjugate and a colloidal gold solution in place of the substrate.

ELISA and spot tests of this kind have been developed for detecting a number of disease-producing organisms. However, a satisfactory test has not yet been developed for tuberculosis produced by the bacterium *Mycobacterium tuberculosis* and leprosy produced by the bacterium *Mycobacterium leprae*, the two most widespread mycobacterial diseases affecting mankind. The difficulty in developing suitable tests has resulted from the fact that *M. tuberculosis* and *M. leprae* produce large numbers of immune response-producing proteins, some of which appear to be common to other microorganisms that may or may not be pathogenic. Hence, positive test results produced by known antigens are generally unreliable (false positives) and other tests have to be carried out to confirm the presence of the tuberculosis or leprosy infections.

Hopes of developing a reliable ELISA test for tuberculosis were heightened recently by the discovery of an *M. tuberculosis* species-specific trehalose-glycolipid provisionally designated as "SL-IV" (F. Papa, et. al., "Serological Specificity of *M. tuberculosis* Glycolipids" (1989), *Acta Leprologica* 7 (Suppl. 1):98–101). An ELISA serological procedure using this protein has been shown to have good potential for the diagnosis of tuberculosis and leprosy. However, SL-IV is extracted from cultures of strains of *M. tuberculosis* and this extraction and the following purification procedures are difficult, time-consuming and expensive. The available quantities of this antigen are therefore quite limited and, moreover, the resulting antigen is a complex mixture of 2,3-trehalose esters. This makes SL-IV of rather limited use for widespread application in ELISA testing.

Trehalose-based glycolipids are found in a variety of structural forms in the lipids of mycobacteria and related bacteria. Serologically active glycolipids extracted from *M. bovis* BCG have been described (Reggiardo et. al., "Serologically Active Glycolipid Families From *Mycobacterium bovis* BCG", *Am. J. Epidemiol.* 10 (1975); 477–486). Three families of glycolipids called A, B and C reacted with sera from patients with tuberculosis and leprosy. Among the antigens studied, one designated Al gave the lowest incidence of false negative serological reactions and was later shown to be 6-0-mycoloyltrehalose (TMM). On the other hand, so-called "cord factor" (6,6'-di-O-mycoloyltrehalose) (TDM), does not seem to be useful as a coating antigen (Goren, M. B., "Mycobacterial Fatty Acid Esters of Sugars & Sulfosugars", Handbook of Lipid Research (Ed. D. J. Hanahan), Vol. 6 (Ed. M. Kates), Glycolipids, Phospholipids and Sulfoglycolipids, pp. 363–396, 1990). Again, however, even the potentially useful antigens have to be extracted from bacterial cultures with the attendant disadvantages.

Accordingly, there is still a need for improved antigens for use in enzyme-linked immunosorbant assays and similar tests for detecting tuberculosis and leprosy.

OBJECTS OF THE INVENTION

An object of the invention is to provide a test capable of diagnosing tuberculosis and/or leprosy with acceptable reliability and specificity using antigen/antibody binding capabilities.

Another object of the invention is to provide glycolipids useful for detecting tuberculosis and leprosy, which glycolipids are relatively stable at ambient temperatures, thus avoiding the need for "cold chain" procedures when storing and distributing the glycolipids.

Still another object of the invention is to provide the components of a test kit for detecting tuberculosis and/or leprosy with acceptable reliability and specificity.

SUMMARY OF THE INVENTION

The invention is based on the finding that various synthetic pseudo cord factor-like glycolipids are suitable for the serodiagnosis of tuberculosis and leprosy. These glycolipids are analogs of natural cord factor (TDM) in that the 6-functional hydroxyl groups of the basic trehalose structure have been transformed either to carboxylic functions or, together with the adjacent —$CH_2$— group, to amido functions.

The invention thus relates to a method of testing for tuberculosis or leprosy in humans or animals, which comprises carrying out an assay on sera from said humans or animals using an antigen to bind antibodies in said sera, wherein said antigen is a pseudo cord factor-like glycolipid having the formula (I) or (II) below:

(I)

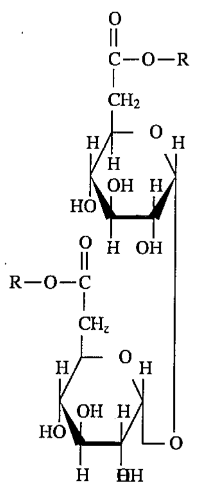

(II)

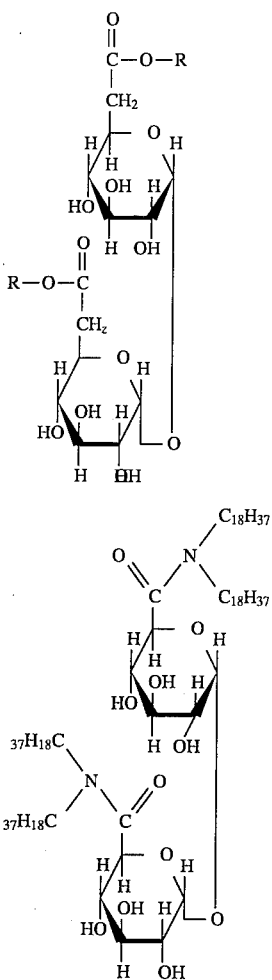

wherein R is a straight chain alkyl group having 15 to 18 carbon atoms.

In the case of the compounds of formula (I), the two R groups are preferably the same, but may be different.

These glycolipids have been found to have high serodiagnostic discriminating activity (sensitivity and specificity) for *M. tuberculosis* and *M. Leprae* and, without wishing to be bound to any particular theory, it is postulated that these synthetic molecules are either cross-reactants of similarly structured native glycolipids of *M. tuberculosis* or that they bear closer resemblance to actual phagosome-lysosome modified antigens than to native bacterial ones.

The glycolipids are also reasonably stable under ambient conditions and can thus be stored and distributed without resort to cold chain techniques.

The invention further elates to solid substrates, such as plate wells or paper substrates, suitable for enzyme-linked immunosorbant assays and spot tests for detecting tuberculosis in humans or animals, which solid substrates have an immobilized coating of a glycolipid of structure (I) or (II) above. These coated substrates can be used as components of ELISA test kits or spot test kits and the invention relates to kits of this kind.

BRIEF DESCRIPTION OF THE DRAWINGS

FIGS. 1(*a*) to 1(*g*) are graphs showing the results of sensitivity and specificity tests carried out for various compounds, as explained in Example 1 below;

FIGS. 2(*a*) to 2(*d*) are similar graphs produced according to Example 2 below;

FIG. 3(A) shows an abbreviated structure of 'true' cord factor (trehalose 6,6' diesters); FIG. 3(B) shows an abbreviated structure of 'mirror' pseudo cord factors (ψCF, esters of trehalose 6,6' dicarboxylic acid); FIG. 3C) shows an abbreviated structure of 'amide' ψCF (amides of 6,6'-diamino trehalose); and FIG. 3(D) shows an abbreviated structure of 'mirror amide' ψCF (amides of trehalose 6,6' dicarboxylic acid);

FIG. 4 shows a summary of syntheses leading to intermediates useful in the construction of various ψ cord factors, in which trehalose is catalytically oxidized to the dicarboxylic acid 1 (TDA) and thence to the dimethyl ester 2 or to hexa-0-acetyl TDA 3 and the corresponding diacid chloride 4; and FIG. 5 shows the syntheses of BDA.TDA, 12, the bis-dioactadecyl amide of 'trehalose dicarboxylic acid'.

DETAILED DESCRIPTION OF THE PREFERRED EMBODIMENTS

Natural cord factor has the partial structure (III) below:

(III)

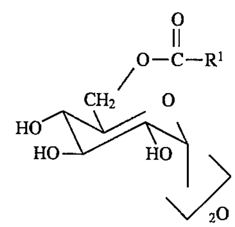

wherein the group $—CO—R^1$ is the mycoloyl group. The mycolyl groups have 60 to 90 carbon atoms forming complex branched chains.

The compounds of the invention differ from natural cord factor in that they have regioinverted ester or amide groups at the terminal positions of the trehalose molecule and in that they contain unbranched lipid chains of intermediate length (15 to 18 carbon atoms). In the case of the esters (I), the structure is a "mirror" arrangement of the natural ester. In the case of the compounds of structure (II), a "mirror" di-N alkyl-substituted amide is present instead of the combined $—CH_2—$ and ester groups.

It should be noted that compounds of structures (I) and (II) have not been detected in the mycobacterial outer cell wall layers, nor indeed elsewhere in nature, and their recognition by antibodies in the sera of tuberculosis patients is thus unexpected.

In the case of the compounds of formula (I), the R group is preferably selected from the following groups:

$n-CH_{15}H_{31}$, pentadecyl $n-C_{16}H_{33}$, hexadecyl $n-C_{17}H_{35}$, heptadecyl $n-C_{18}H_{37}$, octadecyl.

In the case of the compound of formula (II), the octadecyl group $—C_{18}H_{37}$ has a straight chain.

The compounds of the invention of formula (I) can be prepared by the methods described for example by Baer et. al. in "Synthesis of a trehalose homolog, 6-deoxy-α-D-gluco-heptapyranosyl 6-deoxy-α-D-glyco-heptopyranoside, and the corresponding bis(heptosiduronic acid)", *Carbohydr. Res.*, 200:377–389. Two successful synthetic routes are disclosed, starting from α,α-trehalose.

A first route involves chain elongation involving ironcarbonyl chemistry. The protected starting material is reacted with sodium dicarbonylcyclopentadienyliron (NaFp) to form a sugar-iron intermediate which is then treated in situ with bromine and methanol or water to effect carbonyl insertion and methanolysis or hydrolysis. The resulting products can then be saponified.

A second route involves cyanide displacement of hexa-O-acetyl-α,α-trehalose-6,6-ditriflate, followed by O-deacylation and hydrolysis with alkaline hydrogen peroxide.

The amide compound (II) can be prepared by the method of Goren, M. B., et al; "Pseudo Cord Factors: Derivatives of α-D-glucopyranuronosyl (1-1) aD-glucopyranuroside", *Chemistry and Physics of Lipids*, 25 (1979) 209–224, in which derivatives are obtained by Pt-catalyzed oxidation of trehalose, followed by amidation or esterification of the resulting dicarboxylic acids. The test of the Goren et. al. article, which includes a description of the preparation of compound (II) of the present invention (compound (12) of Goren et. al.), is duplicated in part in the Appendix to this specification.

The glycolipids thus formed can be used in the conventional ways for ELISA and related tests. For example, the glycolipids, dissolved in suitable solutions, can be coated onto suitable solid supports, e.g. plate wells, and allowed to dry. The dried coating layers may then be incubated with the test sera following the known procedure. The coated solid substrate may be produced and distributed separately, or may be a component of a test kit. A suitable kit would normally comprise multiple-well (e.g. 96-well) microtiter plates precoated with the immunoreactant, commercially available conjugate, commercially available substrate and a package insert detailing the test procedure.

An example of suitable equipment for s spot test would comprise a strip of paper precoated with immunoreactant, a number of culture tubes (e.g. 12×75 mm), commercially available protein A—colloidal gold conjugate and a package insert detailing the testing procedure.

The effectiveness of the compounds of the invention for the serological diagnosis of tuberculosis and leprosy has been verified as shown in the Examples provided below.

EXAMPLE 1

Sera

One hundred and twelve (112) human sera samples were used in this Example. Of these, fifty six (56) belonged to bacteriologically confirmed tuberculosis patients, of which eight (8) obtained from Buenos Aires, Argentina, were smear negative. Twelve (12) were collected by the Canadian Red Cross and were previously tested as HIV (−) and Hepatitis B (−) and forty four (44) were obtained from a local hospital out-patient clinic. pathologies among the outpatient group included dyspnea, arthritis, pneumonia, connective tissue disorders, vaculitis and peritonitis.

The sera were conserved at either −70° C. or at 4° C. with 0.05% sodium azide.

Antigens

The four preferred esters of structure (I) above and an n-octyl (n-$C_8H_{17}$) analog were synthesized by the method of Baer et. al. mentioned above.

The amide of structure (II) above (i.e. trehalose dicarboxylic acid bis (N,N-dioctadecylamide)) (BDA.TDA) was provided by Dr. M. B. Goren of the National Jewish Center for Immunology and Respiratory Medicine, Denver, Colo. (prepared as described in "Pseudo Cord Factors: Derivatives of α-D-glucopyranuronosyl (1-1) α-D-glucopyranuronoside", *Chemistry and Physics of Lipids*, 25 (1979) 209–224).

Natural cord factor (III) (TDM) was obtained from Dr. Goren and natural SL-IV was obtained from the Pasteur Institute, Paris, France. These were used as natural *M. tuberculosis* antigens for reference.

Enzyme-Linked Immunosorbant Assay (ELISA)

All antigens were solubilized in hexane and 25 μl volumes of solution containing 100 ng of glycolipid were coated onto Dynatech Immulon 3 (trademark) polystyrene microtiter plate wells, and the plates were dried over night at 37° C. Wells treated in a similar manner with 25 μl of hexane without antigen were included for each test serum to check for nonspecific adsorption. All sera were diluted 1/250 in phosphate buffered saline (PBS) containing 0.5% BSA and tested in duplicate.

After saturation overnight at 4° C. with PBS containing 5% BSA, the plates were washed with PBS without Tween (trademark) in a Titertek Microplate Washer (trademark, Flow Laboratories). One hundred (100) μl of diluted human sera were added per well and incubated for 90 minutes. After washings, goat anti-human IgG (H+L)β-galactosidase conjugate (Sera Lab. Ltd., Sussex, England) was added and incubated for 120 minutes.

After further washings, 0-nitrophenyl-β-D-galactoside (ONPG) (SIGMA) substrate was added and the plates were incubated at 37° C. for 60 minutes. The plates were read at 414 nm by a Titertek Multiskan MCC/340 (trademark) reader.

Positive and negative control sera were included in each plate and, for each serum tested, a blank test was performed (uncoated well). The 414 nm values were determined by subtracting test absorbance from blank absorbance. The values were further corrected by a factor obtained by making the absorbance of the well containing the conjugate plus the substrate (v/v, 100 μl) equal to 100% response. The results were confirmed twice.

Data Analysis

Sensitivity, specificity and predictive values were calculated by Bayesian methods (Toman, 1981). To determine means, standard deviations, coefficient of variation as well as sensitivity and specificity at any given cut-off point, data were entered into a LOTUS 123 (trademark) program. At the intersection of sensitivity and specificity curves, their values are equivalent. Intersection points were obtained by varying the value of the cut-off point until the number of false positive and false negative sera became equivalent. Graphs were prepared using the PRINTGRAPH (trademark) program of LOTUS 123.

Results

Table 1 below shows mean values, standard deviations and coefficient of variation of ELISA results obtained in the testing of fifty six (56) sera belonging to the control population (presumably healthy individuals and patients with pathologies other than tuberculosis).

TABLE 1

MEAN, STANDARD DEVIATIONS, POSSIBLE CUT-OFF POINTS AND CO-EFFICIENTS OF VARIATION OF OPTICAL DENSITY (O.D.) VALUES OBTAINED IN THE ELISA SERO DIAGNOSTIC PROCEDURE USING PSEUDO CORD FACTORS AND NATURAL ANTIGENS. DATA DERIVED FROM THE TESTING OF BACTERIOLOGICALLY CONFIRMED TUBERCULOSIS PATIENTS

| ANTIGEN | X* | STD | X + STD** | X + 2STD | X + 3STD | CV%*** |
|---|---|---|---|---|---|---|
| "SL-IV" | 151 | 77 | 227 | 304 | 381 | 51.06 |
| n-pentadecyl | 96 | 54 | 150 | 204 | 258 | 56.74 |
| n-hexadecyl | 117 | 60 | 178 | 238 | 298 | 51.34 |
| n-heptadecyl | 152 | 89 | 241 | 331 | 420 | 59.00 |
| n-octadecyl | 150 | 81 | 232 | 313 | 395 | 54.13 |
| BDA.TDA | 205 | 96 | 300 | 396 | 492 | 46.62 |
| TDM | 77 | 48 | 125 | 174 | 222 | 62.38 |

* X = Mean of 414 * $10^{-3}$;  STD = Standard Deviation; * CV% = Coefficient of Variation %

The data included in this Table are useful to determine possible cut-off points for each of the tested antigens. The variation coefficient measures the relative importance of the standard deviation; thus, low values could indicate better reproducibility or results. Most variation coefficients clustered in the 50 to 65% range; antigens TDM and BDA.TDA yielded the highest and the lowest values, respectively.

A similar table (Table 2 below) was established for the ELISA results obtained in the testing of fifty six (56) sera belonging to tuberculosis patients.

TABLE 2

MEAN, STANDARD DEVIATIONS, AND VARIATION COEFFICIENTS OF OPTICAL DENSITY (O.D.) VALUES OBTAINED IN ELISA SERO DIAGNOSTIC PROCEDURE USING PSEUDO CORD FACTOR AND NATURAL ANTIGENS. DATA RECEIVED FROM THE TESTING OF BACTERIOLOGICALLY CONFIRMED TUBERCULOSIS PATIENTS

| ANTIGEN | X | STD | X + STD | CV% |
|---|---|---|---|---|
| "SL-IV" | 473 | 296 | 768 | 62.54 |
| n-pentadecyl | 422 | 284 | 706 | 67.26 |
| n-hexadecyl | 383 | 280 | 664 | 73.18 |
| n-heptadecyl | 452 | 301 | 753 | 66.70 |
| n-octadecyl | 470 | 321 | 791 | 68.15 |
| BDA.TDA | 648 | 267 | 914 | 41.17 |
| TDM | 278 | 332 | 610 | 119.43 |

The data in this Table show that the highest absorbance results were obtained in the testing of antigen BDA.TDA, the other antigens clustering in the 420 to 470 OD×$10^{-3}$ level range, except for natural cord factor (TDM) which gave 278 OD×$10^{-3}$ and showed the greatest test variation coefficient. Results obtained with the n-octyl analog were not included in the Table because this product was very poorly recognized by the test sera. Alternatively, the n-octyl analog may not dissolve adequately in hexane; or it may be desorbed during contact with the several aqueous systems.

Figure 1B:
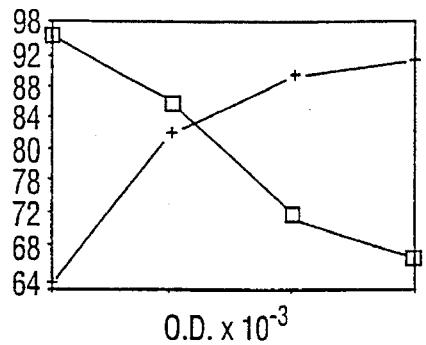
Figure 1C:
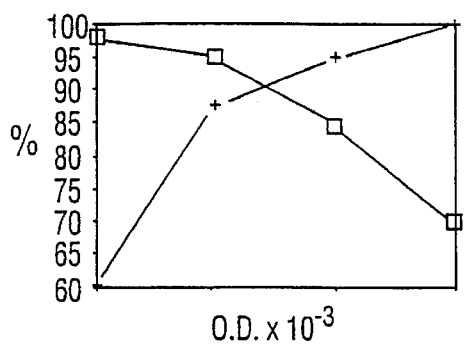
Figure 1D:
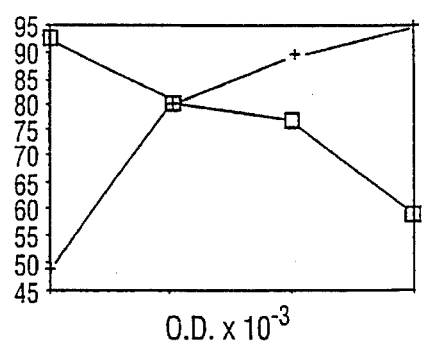
Figure 1E:
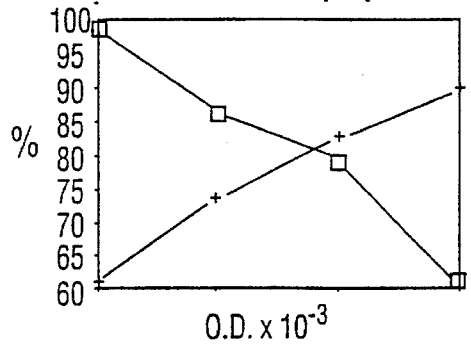
Figure 1F:
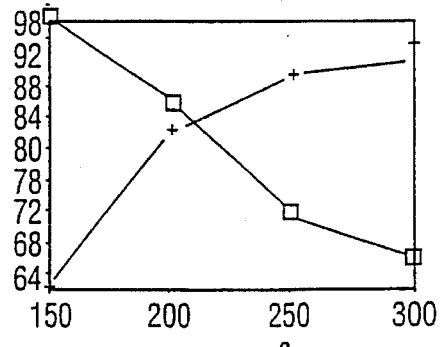
Figure 1G:
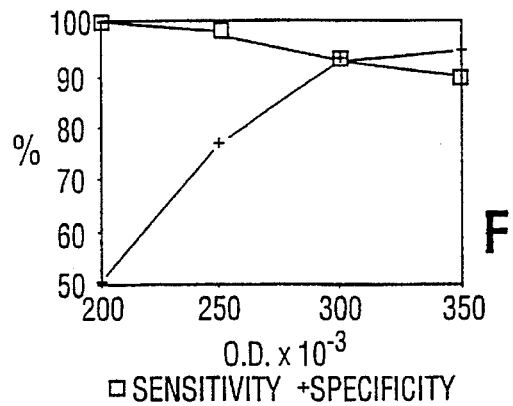

FIGS. 1(a) to 1(g) comprises graphs showing the variation of sensitivity and specificity values as a function of increasing absorbance cut-of values for each of the antigens included in this ELISA evaluation. FIG. 1(A) is for TDM: FIG. 1(B) is for SL-IV; FIG. 1(C) is for the n-pentadecyl ester; FIG. 1(D) is for the n-hexadecyl ester; FIG. 1(E) is for the n-heptadecyl ester; FIG. 1(F) is for the n-octadecyl ester; and FIG. 1(G) is for BDA.TDA. The point where the sensitivity and specificity curves meet, called an intersect, determines the cut-off absorbance value at which sensitivity and specificity become equivalent; i.e. the cut-of value at which the test yields an equal number of false positive and false negative results.

It is evident from the graphs of FIG. 1 and from the determined intersect values that among all the antigens tested, BDA.TDA showed the highest serodiagnostic discriminatory power, with 93 specificity and sensitivity values. Natural cord factor (TDM) showed the lowest discriminatory power whereas the rest of the antigens tested cluster in the acceptable 80 to 90% range (Table 3).

TABLE 3

SENSITIVITY AND SPECIFICITY VALUES CALCULATED AT THE INTERSECTION OF CURVES IN FIG. 1. CUT-OFF POINTS VALUES EXPRESSED AS 414 * $10^{-3}$ UNITS

| ANTIGEN | 414 INTERSECT * $10^{-3}$ | SENS. & SPEC. % |
|---|---|---|
| "SL-IV" | 229 | 83.93 |
| n-pentadecyl | 179 | 89.29 |
| n-hexadecyl | 150 | 80.36 |
| n-heptadecyl | 230 | 80.36 |
| n-octadecyl | 208 | 82.14 |
| BDA.TDA | 300 | 92.86 |
| TDM | 80 | 58.93 |

Finally, it is interesting to note that the calculated intersect values are identical or very close to Mean+1 Standard deviation values for all antigens tested except cord factor.

EXAMPLE 2

Sera

One hundred and thirty-seven (13 g) human sera were tested in this study, of which 81 were taken from leprosy patients. According to the Ridley-Jopling classification, 10 sera belonged to the polar tuberculoid (TT) form, 16 to the polar lepromatous (LL) form, 8 to the borderline tuberculoid (BT) form, 7 to the indeterminate (IND) form, 8 to the mid-borderline (BB) form and 7 to the borderline lepromatous (BL) form. Twenty-five (25) other human leprosy sera were obtained from the Institute Fame Pereo in Port au Prince, Haita; 9 were classified as multibacillary and 16 paucibacillary. The other 58 sera were obtained from the Canadian Red Cross, and from a local hospital's out-patient clinic. The latter sera belonged either to healthy individuals or to patients suffering from a variety of diseases other than tuberculosis or leprosy.

Antigens

Trehalose dicarboxylic acid bis (N,N-dioctadecylamide) (BDA.TDA) was provided by one of the inventors (see Goren M. B. and Jiang K. S., "Psuedo Cord Factors: Derivatives of α-D-glucopyranuronosyl (1-1) α-D-glucopyranuronoside," *Chemistry and Physics of Lipids*, 25, (1979), 209–224) while SL-IV was obtained from the Pasteur Instituted of Paris.

Enzyme-Linked Immunosorbent Assay (ELISA)

Twenty five (25) microliters of hexane containing 100 ng of glycolipid antigen were coated onto Dynatech Immulon (Trademark) polystyrene microtiter plate wells using a single pipet and dried at 37° C. Wells similarly treated but without antigen were used to check for non-specific serum absorption. After overnight saturation at 4° C. with phosphate buffer saline (PBS) containing 5% bovine serum albumin (BSA), the plates were washed with PBS without Tween (Trademark) in a Titertek Microplate Washer (Trademark, ICN Biomedicals, Inc., Huntsville, Ala., U.S.A.). Test sera, diluted 1/250 in PBS were added in 100 microliter volumes into each well. After 90 minutes of incubation followed by further washing, goat antihuman IgG and IgM (H+L) β-galactosidase conjugates (Biosys, Compiegne, France) were added to the wells which were then incubated for 120 minutes. After an additional washing, o-nitrophenyl-β-D-galactoside (ONPG) (SIGMA, St. Louis, Mo., U.S.A.) substrate was added and the plates were incubated at 37° C. for 60 minutes. Plates were read at 414 nm by a Titertek Multiskan MCC/340 reader (Trademark, ICN Biomedicals, Inc., Huntsville, Ala., U.S.A.). Δ414 O.D. values were determined by subtracting blank absorbance values from test absorbance values and by using a correction factor obtained by making the absorbance in wells containing the conjugate plus the substrate (v/v, 100 microliters), equal to the 100% response; results were confirmed once.

Data Analysis

Sensitivity, specificity and predictive values were calculated by Bayesian methods. To determine mean, standard deviation, coefficient of variation as well as sensitivity and specificity values at any chosen cut-off point, data were entered into a "LOTUS 123" (Trademark) specially designed program. In order to compare the antigens cut-off points were chosen yielding maximum specificity values. Graphs were prepared using the "PRINTGRAPH" (Trademark) program of "LOTUS 123". Dual modes of testing were compared and analyzed with a special designed LOTUS program in which antigens are compared one on one and the Bayesian characteristics calculated accordingly.

Results

Table 4 shows mean values, standard deviation and coefficient of variation for sera from the leprosy patient group and for sera belonging to presumably healthy individuals and patients suffering from pathologies other than tuberculosis.

TABLE 4

MEANS, STANDARD DEVIATION AND COEFFICIENT OF VARIATION OF ELISA TESTING OF LEPROSY (+) AND NON-LEPROSY (−) HUMAN SERA. UNLESS OTHERWISE INDICATED, THE DATA EXPRESSED ARE IN 414 · $10^{-3}$ UNITS

|  | IgG SLIV | IgG BDA | IgM SLIV | IgM BDA |
|---|---|---|---|---|
| MEAN "−" | 77 | 197 | 65 | 188 |
| STD | 54 | 103 | 67 | 128 |
| MEAN + 1 STD | 131 | 301 | 132 | 316 |
| MEAN + 2 STD | 184 | 404 | 199 | 444 |
| CV % | 69.8% | 52.5% | 104.3% | 68.3% |
| MEAN "+" | 307 | 524 | 264 | 332 |
| STD | 234 | 279 | 224 | 261 |
| CV % | 76.2% | 53.3% | 84.9% | 78.8% |

The means values of non leprosy sera are higher for the synthetic antigen BDA.TDA than for the natural antigen SL-IV, in both the IgG and IgM antibody classes. However, the coefficient of variation was almost twice as high for SL-IV than for BDA.TDA. The Table also shows that sera belonging to leprosy patients recognize the synthetic antigen more strongly then the natural antigen (O.D. 0.524 vs. O.D. 0.307) but only in the IgG class and that the coefficient of variation for the synthetic product is lower than that of SL-IV (53% vs. 76%).

Figure 2A:
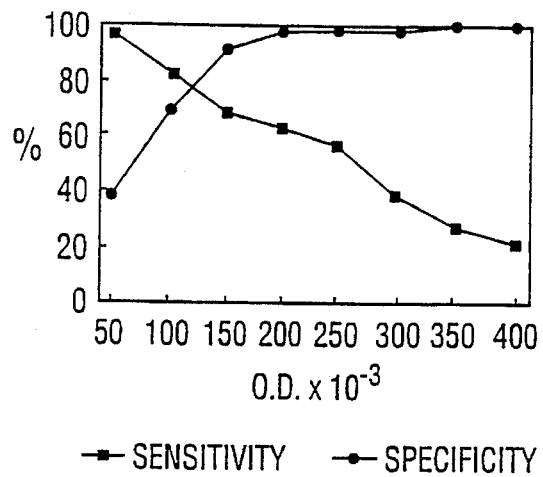
Figure 2B:
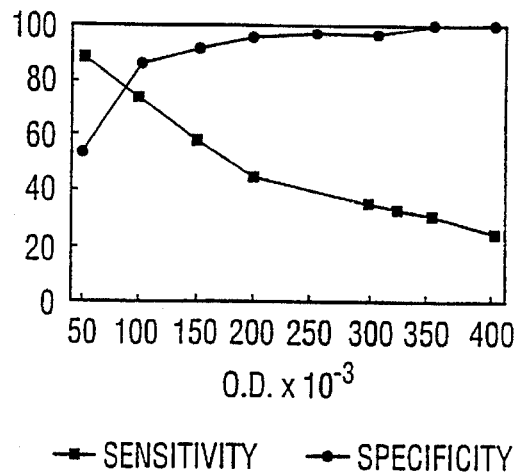
Figure 2C:
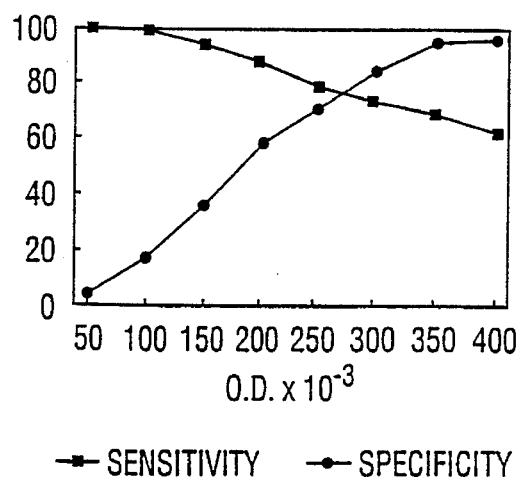
Figure 2D:
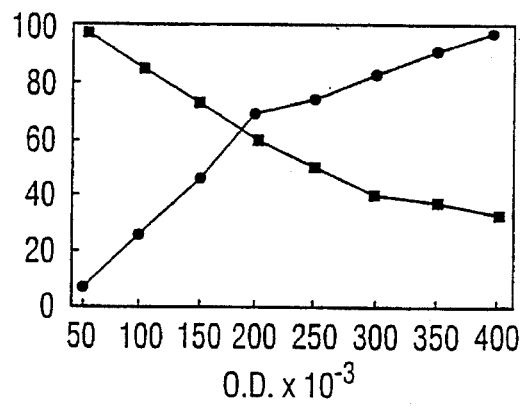
Figure 3A:
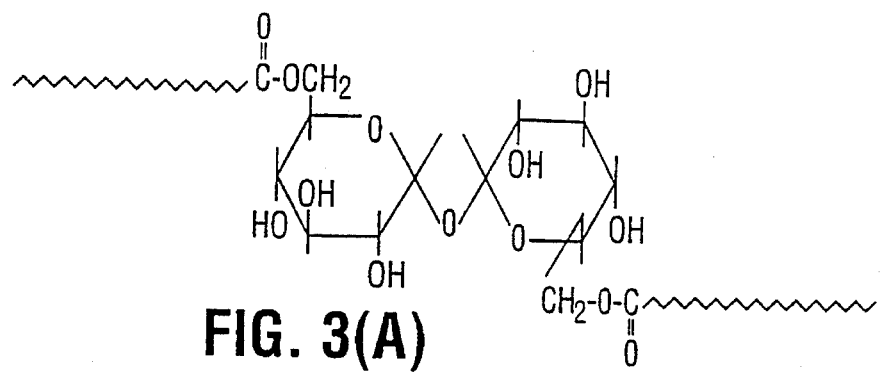
Figure 3B:
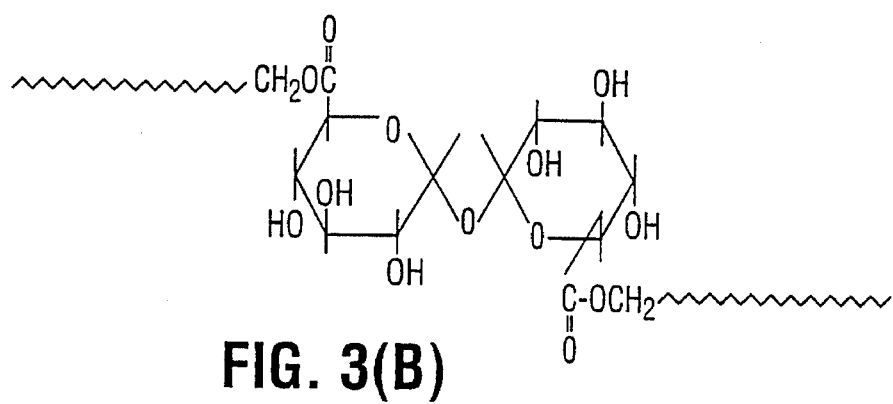
Figure 3C:
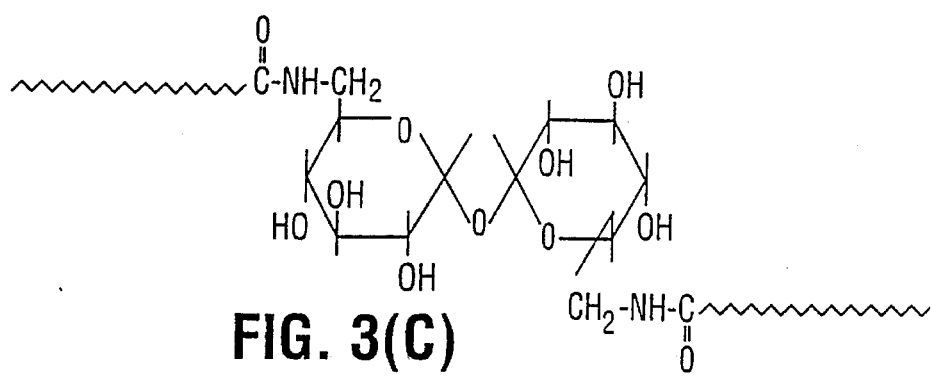
Figure 3D:
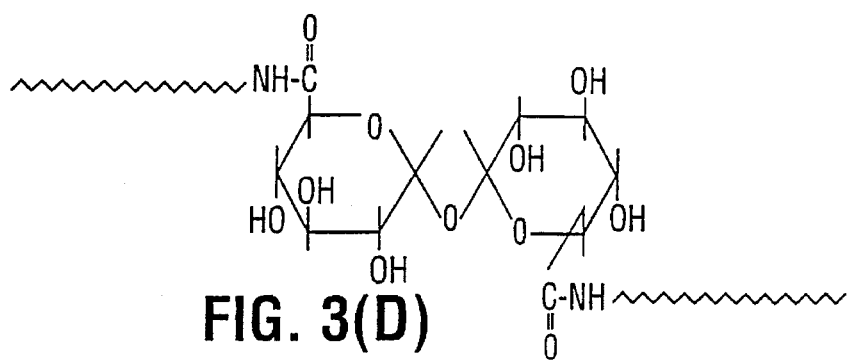

The discriminating power of ELISA testing of these two substances in the serodiagnosis of leprosy in the IgG and IgM classes is depicted in FIGS. 2(A)–2(D) which shows the variation of the sensitivity and specificity parameters as a function of the increasing O.D. values of the cut-off point. FIG. 2(A) is for IgG SL-IV; FIG. 2(B) is for IgM SL-IV; FIG. 2(C) is for IgG oDA.TDA; and FIG. 2(D) is for IgM BDA.TDA.

High cut-off points i.e. Mean plus two standard deviations, can be chosen to maximize the specificity of the test and to facilitate the comparison of the performance of the antigens (Table 5).

TABLE 5

SENSITIVITY (SENS) SPECIFICITY (SPEC), PREDICTIVE VALUE OF POSITIVITY PVP PREDICTIVE VALUE OF NEGATIVITY OF ELISA TESTING OF SL IV AND BDA.TDA CUT-OFF POINTS EXPRESSED IN 414 · $10^{-3}$ UNITS

| BAYESIAN ANALYSIS | IgG SLIV | IgG BDA | IgM SLIV | IgM BDA |
|---|---|---|---|---|
| SENS | 63.0% | 63.0% | 44.4% | 26.0% |
| SPEC | 98.3% | 96.5% | 94.8% | 96.5% |
| PVP | 98.0% | 96.2% | 92.3% | 91.3% |
| PVN | 65.5% | 65.1% | 55.0% | 48.3% |
| CUT OFF POINT | 184 | 404 | 199 | 444 |

The two antigens have similar capabilities in the IgG class, i.e. BDA.TDA shows a sensitivity of about 63% at a specificity of about 97% with the cutoff value at O.D. 0.350 versus about 63% at a specificity of about 98% respectively for SL-IV with the cutoff value at O.D. 0.150. The data obtained in the IgM class using the corresponding cut-off values yielded lower sensitivity levels, especially in the case of BDA.TDA.

Of the 81 leprosy sera included in this study, 41 can be considered as paucibacillary (TT, BT, IND) and 40 as multibacillary (BB, BL, LL). Table 6 shows the mean, standard deviation and coefficient of variation obtained in sera from multibacillary and paucibacillary leprosy patients with both SL-IV and BDA.TDA.

TABLE 6

MEAN VALUES, STANDARD DEVIATION (STD) AND COEFFICIENT OF VARIATION (CV) OF THE ELISA TESTING OF PAUCIBACILLARY AND MULTIBACILLARY LEPROSY SERA. DATA, UNLESS OTHERWISE INDICATED, ARE EXPRESSED IN 414 × 10⁻³ UNITS

| ORIGIN | IgG SLIV | IgG BDA | IgM SLIV | IgM BDA |
|---|---|---|---|---|
| Pauci-bacillary | | | | |
| MEAN | 258 | 527 | 224 | 325 |
| STD | 188 | 261 | 180 | 229 |
| CV % | 73.0% | 49.6% | 80.1% | 70.5% |
| Multi-bacillary | | | | |
| MEAN | 358 | 521 | 304 | 338 |
| STD | 264 | 297 | 255 | 290 |
| CV % | 73.7% | 57.0% | 84.0% | 85.9% |

It is evident from this Table that the level of antigen recognition is higher in multibacillary patients than in paucibacillary patients for SL-IV in both the IgG and IgM antibody classes. This is not the case for BDA.TDA since the mean values vary only as a function of antibody class i.e. IgG means are higher than IgM means, but there are not differences in the level of recognition between paucibacillary and multibacillary disease.

At the cut-off points which were chosen above and for data obtained in the IgG class, SL-IV detected above 61% (25/41) of the paucibacillary cases and about 65% (26/40) of the multibacillary cases whereas BDA.TDA detected about 59% (24/41) and about 63% (25/40) respectively.

EXAMPLE 3

Tuberculosis is still a serious worldwide public health problem with 8 million cases reported in 1990, it is calculated that one-third of the world population is infected with *M. tuberculosis* (3). Most of the cases are found in developing countries which account for approximately 95% of all cases. The diagnosis still relies on the detection of *M. tuberculosis* by smear staining with Ziehl-Neelsen and on the culturing of the ethiological agent in the appropriate media. Efforts have been made to find better diagnostic procedures because although smear microscopy method is rapid, it lacks sensitivity (7) and because the culture—the gold standard for diagnosis—takes about 6 to 8 weeks.

Methods proposed to expedite the diagnosis of tuberculosis include mycobacterial genomic DNA analysis (4), the detection of *M. tuberculosis* antigens (3, 14) and the measurement of the immune response. Of these methods the more affordable for the clinical laboratory are the indirect ELISA tests which detect antigens of *M. tuberculosis* such as polysaccharides (13), proteins (1,2) and glycolipids (2,6,7, 8,9).

We have recently developed an ELISA test which uses a synthetic glycolipid, i.e. BDA.TDA, useful in the serodiagnosis of tuberculosis and leprosy. This, along with the related "spot test" is disclosed in our co-pending U.S. patent application Ser. No. 07/881,193. It has not become apparent that this test needed simplification to be useful in the field where most of the diagnosis of tuberculosis is made. We decided therefore to develop an improved and rapid Dot-Blot assay ("spot test") kit conjugate is enhanced by a rabbit anti-human serum.

MATERIAL AND METHODS

Antigen

BDA.TDA was synthesized by M. B. Goren and stored at −20° C. at a concentration of 1 mg/ml in a chloroform-methanol 1:2 solution.

Sera

The sera samples were obtained with prior consent from patients attending the Hospital Universitario "Dr. Jose Eleuterio González", in Monterrey, N.L., Mexico. The sera were stored at −20° C. and sent to Ottawa where they were stored in aliquots at −70° C. until use. The samples were taken before the beginning of chemotherapy. The patients were diagnosed based on clinical and radiological evaluation as well as by smear staining and culturing of sputum samples. As negative controls, sera from healthy subjects without any symptoms of pulmonary disease were used. Most of these were obtained from students from the School of Medicine, U.A.N.L., the majority of which had been BCG vaccinated in the past. The sera were stored in the same conditions as above and were used less than 1 year from the time they were taken.

Dot-Blot Assays

Since the chloroform-methanol glycolipid solutions are corrosive for the nitrocellulose paper, we evaporated (60 µl) the chloroform-ethanol solution and reconstituted it with hexane (150 µl) which is harmless for the nitrocellulose paper. From this working solution, 2.5 µl were spotted onto nitrocellulose strips (approximately 10×4 mm) which were allowed to dry at room temperature. The strips were rinsed briefly in PBS, pH 7.2, incubated for 1 hour at 37° C. or overnight at 4° C. in blotto (5% skim milk [BBL] in PBS with 0.05% sodium azide) to block the residual binding sites on the paper.

The strips were rinsed for 10 min in PBS and then incubated with the sera diluted 1:80 in blotto for 30 min at 37° C. After incubation, the strips were washed with at least four volume changes of PBS and further incubated with a rabbit anti-human serum (rabbit immunoglobulins to human, Dako-Immunoglobulins, Carpinteria, Calif.) diluted 1:500 in blotto for 10 min at 37° C. The strips were washed with PBS and incubated with a complex protein A-gold (Sigma, Protein A-20 nm colloidal gold labelled) with an absorbance of 5.3 at 520 nm, for 5 min at room temperature. The strips were washed four times and allowed to dry on a filter paper. A red clear spot on the site where the antigen was spotted was considered positive. The absence of reaction or a trace result was considered negative.

RESULTS

Selection of the Matrix Support

We observed that of the various support materials tested under the conditions of our study, only nitrocellulose paper (0.45 µm pore size, BioRad) developed a sport when tested with a positive serum. The other matrices, which are all synthetic resin based membrane materials, showed no reaction, reflecting perhaps the lack of binding of the glycolipids to the membranes. It will be appreciated by those skilled in the art that other similar paper materials commonly used for such tests would also be useful.

Dot Blot Assay

We checked several coating doses of glycolipid by testing a positive control serum with an ELISA O.D. of 0.8 and a negative serum with O.D. of less than 0.1. We considered as optimal coating dose the concentration that gave a clear signal with the positive control and still remained negative with sera derived from healthy individuals. We selected 1 μg of BDA.TDA per spot as the best coating dose.

To detect the antigen-antibody reaction, we originally used a protein A-gold conjugate immediately after the incubation with the sera. However, the signal observed was weak and not very clear. To increase the sensitivity of the assay, we used a second incubation with a rabbit anti-human serum, increasing the signal significantly.

Once determined, the optimal coating dose, the incubation periods and optimal detection system, we assayed this system with sera from patients with tuberculosis and healthy subjects as negative controls. The assay was done at least twice, and we scored as positive only those test giving clear signals. Table 7 below shows the results of parallel testing of the sera with both β-galactosidase indirect ELISA and the above described Dot-Blot. It is evident from these results that this much simplified diagnostic procedure is almost as sensitive as the original indirect ELISA.

TABLE 7

REACTION OF HUMAN SERA IN THE INDIRECT
ELISA ASSAY AND IN THE DOT-BLOT TEST
OF BDA.TDA

| SERUM | O.D. IN THE ELISA TEST | REACTION IN THE DOT-BLOT TEST |
|---|---|---|
| 1 | 0.000 | – |
| 2 | 0.037 | – |
| 3 | 0.049 | – |
| 4 | 0.064 | – |
| 5 | 0.074 | – |
| 6 | 0.101 | – |
| 7 | 0.105 | – |
| 8 | 0.114 | – |
| 9 | 0.120 | – |
| 10 | 0.159 | – |
| 11 | 0.267 | – |
| 12 | 0.272 | – |
| 13 | 0.285 | – |
| 14 | 0.511 | + |
| 15 | 0.513 | – |
| 16 | 0.519 | + |
| 17 | 0.938 | ++ |
| 18 | 0.996 | + |
| 19 | 1.277 | + |
| 20 | 1.291 | ++ |
| 21 | 1.378 | ++ |

Cut-off point for ELISA: O.D. 0.300

DISCUSSION

Several antigens of *Mycobacterium tuberculosis* have been found to be useful in the serodiagnosis of the clinical disease (1,2,6). Among them, some glycolipids have been shown to be immunogenic (9,10,11). By using ELISA, it was found that one of them—BDA.TDA a synthetic pseudo-cord factor—was useful in the serodiagnosis of tuberculosis and leprosy (8,9). Although the ELISA testing system is very practical and sensitive, it is not always available in high TB prevalence countries especially in the peripheral health units where most of the tuberculosis cases are diagnosed. In other infectious diseases, the ELISA system has been advantageously replaced by a Dot-Blot method with protein A-gold conjugate. By using a protein A-gold system the method is considerably simplified and by using a second antibody again human IgGs raised in rabbit—a species that also binds protein A—the reaction between the Fc fragment of IgG with protein A is enhanced.

REFERENCES

1) Charpin, D., Herbault, H., Gevaudan, M. J., Saadjian, M., de Micco, P., Arnaud, A., Vervloet, D. and Charpin, J. (1990) Value of ELISA using A60 antigen in the diagnosis of active pulmonary tuberculosis. Am. Rev. Respir. Dis. 142, 380.

2) Cruaud, P., Yamashita, J. T., Martin-Casabona, N., Papa, F. and David, H. L. (1990) Evaluation of a novel 2,3-diacyl-trehalose-2'-sulphate (SL-IV) antigen for case finding and diagnosis of leprosy and tuberculosis. Res. Microbiol. 141, 679.

3) Kochi, A. (1991) The global tuberculosis situation and the new control strategy of the World Health Organization. Tubercle. 72, 1.

4) Kox, L. F. F., Rhienthong, D., Medo Miranda, A., Udomsantisuk, N., Ellis, K., van Leewan, J., van Heusden, S., Kuijper, S., and Kolk, A. H. J. (1994) A more reliable PCR for detection of *Mycobacterium tuberculosis* in clinical samples. J. Clin. Microbiol. 32: 672–678.

5) Lipsky, B. A., Gates, J., Tenover, F. C. and Plorde, J. J. (1984) Factors affecting the clinical value of microscopy for acid-fast bacilli. Rev. Infect. Dis. 6, 214.

6) Laszlo, A., Baer, H. H. , Goren, M. B., Handzel, V., Barrera, L. and de Kantor, I. N. (1992) Evaluation of synthetic pseudo cord-factor-like glycolipids for the serodiagnosis of tuberculosis. Res. Microbiol. 143, 217.

7) Laszlo, A., Cruaud, P., Goren, M. B., Handzel, V., Papa, F. and David, H. L. (1992) Comparison of Bis-di-octadecylamide of trebalose dicarboxylic acid (BDA.TDA) with glycolipid SL-IV as ELISA antigens for the serodiagnosis of leprosy. Int. J. Lepr. 60, 376.

8) Martin-Casabona, N., Gonzalez Fuente, T., Papa, F., Rosselló Urgell, J., Vidal Plá, R., Codina Grau, G., and Ruiz Camps, I. (1992) Time course of anti-SL-IV immunoglobulin G antibodies in patients with tuberculosis and tuberculosis-associated AIDS. J. Clin. Microbiol. 30, 1089.

9) Papa, F., Cruaud, P. and David, H. L. (1989) Antigenicity and specificity of selected glycolipid fractions from *Mycobacterium tuberculosis*. Res. Microbiol. 140, 569.

10) Papa, F., Luquin, M. and David, H. L. (1992) DOT-ELISA for detection of phenolic glycolipid PGL-TB1 and diacyl-trehalose antigens of *Mycobacterium tuberculosis*. Res. Microbiol. 143, 327.

11) Ridell, M., Wallterström, G., Minnikin, D. E., Bolton, R. C. and Magnusson, M. (1992) A comparative serological study of antigenic glycolipids from *Mycobacterium tuberculsosis*. Tubercle. 73, 101.

12) Sada, E., Lavenia, E. F. and Daniel, T. M. (1990) An ELISA for the serodiagnosis of tuberculosis using a 30,000-Da native antigen of *Mycobacterium tuberculosis*. J. Infect. Dis. 169: 928–931.

13) Sada, E., Brennan, P. J., Herrara, T. and Torres, M. (1990) Evaluation of lipoarabinomannan for the serological diagnosis of tuberculosis. J. Clin. Microbiol. 28, 2587.

14) Brooks, J. B., Danshvar, M. I., Haberberger, R. L. and Mikhail, I. A. (1990) Rapid diagnosis of tuberculous meningitis by frequency-pulsed electron-capture gas-liquid chromatography detection of carboxylic acids in cerebrospinal fluid. J. Clin. Microbiol. 28: 989–997.

APPENDIX

The following is a duplication in part of an article by Goren et. al., Chemistry and Physics of Lipids, 25 (1979) 209–224.

PSEUDO CORD FACTORS: DERIVATIVES OF α-D-GLUCOPYRANURONOSYL (1-1) α-D-GLUCOPYRANURONOSIDE.

MAYER B. GOREN* and KUO-SHII JIANG

Figure 4:
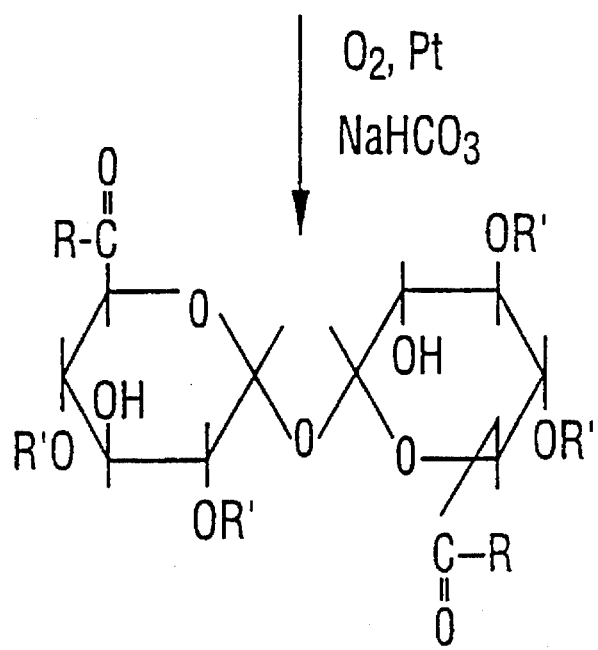

From FIG. 3, it is clear that what we have termed 'mirror' pseudo cord factors and 'mirror amide' ψ CF are based upon a core-carbohydrate α-D-glucopyranuronosyl (1-1) α-D-glucopyranuronoside, 1-'trehalose dicarboxylic acid', or 'TDA', whose synthesis we have described [25]. As shown in FIG. 4, this 'dimer' of glucuronic acid is obtained by platinum-catalyzed oxidation of trehalose according to methods that Mehltretter has described for various other starting substances [26]. From TDA, the dimethyl ester, 2, and the hexa O-acetyl diacid, 3, and diacid chloride, 4, were prepared [25] as reactive intermediates for the synthesis 'mirror' and 'mirror amide' ψ CF.

The preparation of hexa-0-acetyl TDA, 3, and the diacid chloride, 4, (FIG. 4) was described earlier [25]. By means of 4, more complex amides of TDA were obtainable than could be synthesized from the dimethyl ester, 2, by aminolysis.

Figure 5:
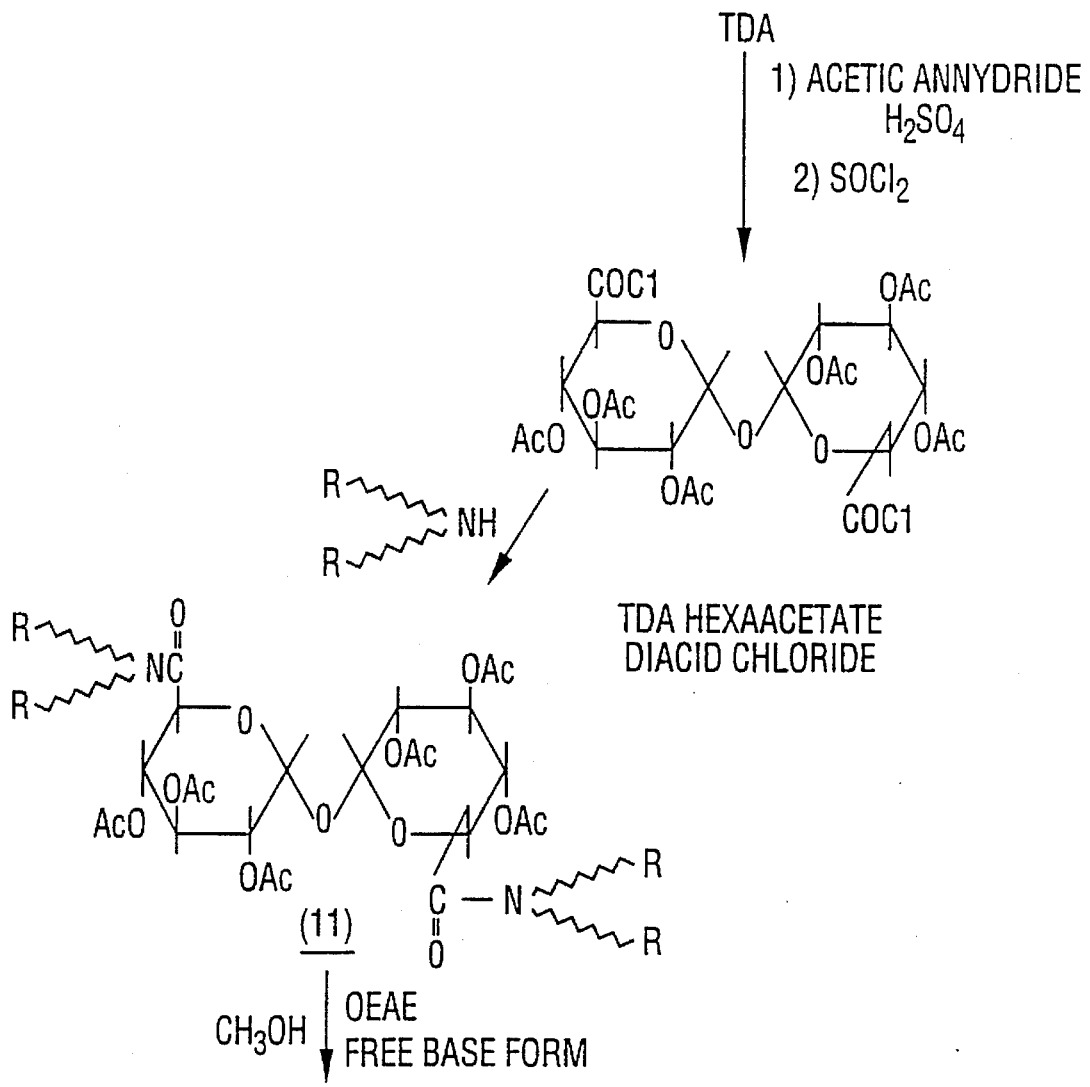
Figure 5:
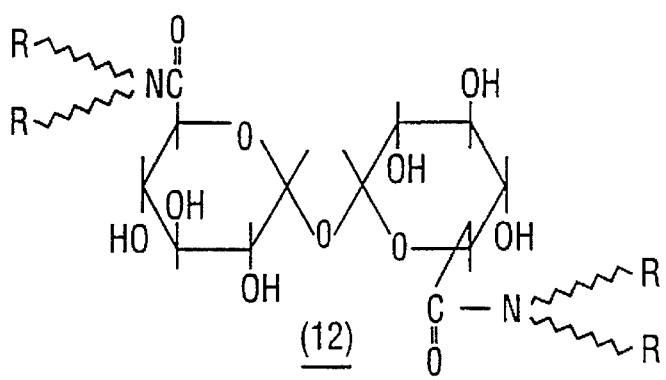

Bis-N-di-n-octadecylamide of 'trehalose dicarboxylic acid': 'BDA.TDA', 12 As shown in FIG. 5, with a secondary amine ('Armeen-2HT', a commercial product of Armak Chemical Division, consisting principally of di-n-octadecylamine, but with some lower homologs), the diacid chloride hexaacetate was readily converted into the symmetrical diamide hexaacetate, 11. The acetyl groups were removed either by solvolysis in $CH_3OH$ on a column of DEAE cellulose (free base form [33,34]); or by methanolysis in the presence of $NaOCH_3$. The deacetylated product, 12, with mobility in thin layer chromatography similar to natural cord factor, is recovered from the deacetylation mixture by chromatography on a column of DEAE cellulose (acetate form) and cellulose in an overall yield of approx. 50% based on hexaacetyl TDA This choice of a secondary amine for condensation with TDA was predicated on our intent to prepare 'mirror amide' ψ cord factors of higher molecular weight, and to mimic more closely the α-branched structure of natural cord factors, which in this analog is conferred by the two alkyl groups of the amine. The availability of an inexpensive commercial product, albeit not the ψ cord factors, if they find utility as substitutes for the natural glycolipid, which is obtainable only with difficulty. Indeed although the 'bis-dioctadecyl amide of trehalose dicarboxylic acid' (12, BDA.TDA) had low toxicity in mice, it was nevertheless an excellent substituted for cord factor in exhibiting comparable antitumor activity in the strain 2 guinea pig line-10 tumor system of Rapp and colleagues [28].

MATERIALS AND METHODS

All microanalyses were carried out by the Galbraith Laboratories, Knoxville, Tenn.

The synthesis and properties of α-D-glucopyranuronosyl (1-1) α-D-gluocopyranuronoside, 1, its dimethyl ester, 2, hexa-0-acetate, 3, and hexa-0-acetate dicarboxylic acid chloride, 4, have been previously described [25].

α-D-glucopyranuronosyl(1-1) α-D-glucopyranuronoside, bis-N-(di-1,1'-octadecyl)amide (BDA.TDA), 12. The diacid chloride was prepared [25] from 0.18 g hexaacetyl TDA. Di n octadecylamine ('Armeen 2HT') (0.54 g) in 5 ml benzene was added to the acid chloride and the mixture held at reflux for 1.5 h. The mixture was evaporated to dryness and extracted three times with 10–15 ml portions of hexane to dissolve the reaction product and some excess amine. The hexane-soluble product was recovered by evaporation, dissolved in 5 ml $CH_3OH/CHCl_3$ (2:1) and, for deacetylation, introduced into a column of cellulose and DEAE-cellulose (free base form) (5.4–2.7 g) for 18 h contact, when the column was eluted with the same solvent. Deacetylation was complete (infrared spectrum). The bis-N-di-n-octadecylamide of trehalose dicarboxylic acid (BDA:TDA) was purified by chromatography in the same cellulose-DEAE cellulose column in the acetate form. The product was loaded in hexane solution and eluted with: (1) 200 ml hexane; (2) 300 ml hexane/$CHCl_3$ (1:1); (3) 1500 ml $CHCl_3$; (4) 150 ml $CHCl_3$/5% $CH_3OH$; (5) 150 ml $CHCl_3$/10% $CH_3OH$. Homogeneous BDA.TDA was recovered from the $CHCl_3$ eluates (0.171 g) and an additional 0.041 g was recovered by rechromatography of the earlier fractions, (yield 54%). The $CHCl_3/CH_3OH$ eluates contained both BDA.TDA and a much more polar product judged to be the monoamide of TDA and dioctadecyl amine. BDA.TDA was recrystallized from ethanol to yield a waxy product. It sinters at approx. 50° C. and gives nondescript melting from 105° C., yielding a clear viscous melt at about 135° C. $[α]^{24}_D$+45 (c=1.47 in $C_2H_3OH/CHCl_3$, 2:1).

NMR Data—in $CDCl_3$: carbohydrate protons unrelaxed with broad clumped peaks from τ 4.82 to 6.62. A similar aspect is presented in $CDCl_3$ solutions of cord factor (H. Fales, pers. commun.). The protons in the aliphatic amine chains gave appropriate peaks at τ 8.74 and 9.1. There was no evidence of residual acetate (τ7.92).

Found: C, 72.53%; H, 11.99%; N, 2.03%. Calc. for $C_{84}H_{164}N_2O_{11}$: C, 73.20%; H, 11.95%; N, 2.11%.

The infrared spectrum of BDA.TDA (not shown) has many features of the spectrum of native cord factor: broad deep hydroxyl absorption peaking at about 3300 $cm^{-1}$ and deep bands associated with the $CH_2$ stretching vibration at 2850–2900 $cm^{-1}$ that are essentially absent in the spectrum of TDA and simple derivatives; a single carbonyl (amide)

band at about 1640 cm$^{-1}$ in the region 1000–1200$^{-1}$ fingerprint absorptions associated with trehalose as well as the weak trehalose band at 805 cm$^{-1}$ [34]. Thus the contributions of both moieties of the ψ cord factor are prominent.

REFERENCES

1 H. Bloch, J. Exp. Med., 91 (1950) 197.
2 N. B. Goren and K. S. Jiang, submitted.
3 C. L. Mehltretter, Adv. Carbohydr. Chem., 8(1953)231.
4 H. J. Rapp, Israel J. Med. Sci., 9(1973)366.
5 M. B. Goren and O. Brokl, Recent Results Cancer Res., 47(1974)251.
6 M. B. Goren, O, Brokl, P. Roller, H. M. Fales and B. C. Das, Biochemistry, 15 (1976)2728.

We claim:

1. A spot test kit useful for the serodiagnosis of tuberculosis in a human or animal suspected of being exposed to *Mycobacterium tuberculosis*, comprising:

at least one tube for collecting a blood sample;
protein A-colloidal gold conjugate;
a rabbit anti-human immunoglobulin;
instructions for carrying out the test procedure; and
a strip of test paper coated with a glycolipid having the following formula:

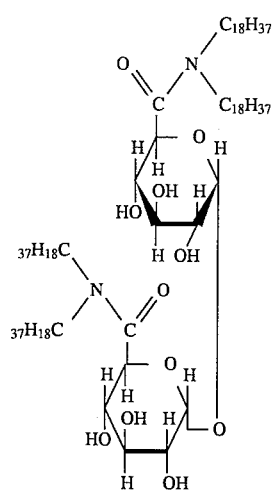

2. A spot test kit according to claim 1, wherein the test paper is nitrocellulose paper.

3. A spot test kit according to claim 2, wherein the amount of glycolipid coating is about 1 μg.

* * * * *